United States Patent [19]

Kerr

[11] Patent Number: 5,763,234
[45] Date of Patent: Jun. 9, 1998

[54] SECOSTEROIDS, AND METHOD FOR PRODUCING SAME

[75] Inventor: Russell G. Kerr, Boca Raton, Fla.

[73] Assignee: Florida Atlantic University, Boca Raton, Fla.

[21] Appl. No.: 687,270

[22] Filed: Jul. 25, 1996

[51] Int. Cl.$^6$ .............. C12P 15/00; C12P 7/42; C12P 7/26

[52] U.S. Cl. ............ 435/127; 435/146; 435/148

[58] Field of Search ............... 435/148, 127, 435/146

[56] References Cited

PUBLICATIONS

Ochi, M. et al. (1991) "Calicoferols A and B, Two Novel Secosterols Possessing Brine–Shrimp Lethality from the Gorgonian Calicogorgia sp." Chemistry Letters, pp. 427–430.

D'Auria, M.V., L. Minale, R. Riccio (1993) "Isolation and Synthesis Of A New 9.11–Secosterol From The Sponge *Spongia Officinalis*" Journal of Natural Products 57(9):1200–1226.

He, Haiyin et al. (1995) "New Antiproliferative And Antiflammatory 9,11–Secosterols from the Gorgonian Pseudopterogorgia sp." Tetrahedron 51(1):51–58 Jan.–Feb.

D'Auria, Maria Valeria, Luigi Minale and Raffaele Riccio (1993) "Polyoxygenated Steroids of Marine Origin" Chem. Rev. 93:1839–1895.

*Primary Examiner*—Herbert J. Lilling
*Attorney, Agent, or Firm*—Quarles & Brady

[57] ABSTRACT

A fortified enzyme preparation of the gorgonian *Pseudopterogorgia americana* has been developed which efficiently transforms a variety of sterols to their 9(11)-secosteroid derivative in high yield. NAD, NADP, and glutamate dehydrogenase are key additives in this enzymatic conversion. In addition to naturally-occurring metabolites, novel secosteroids have been prepared.

3 Claims, 1 Drawing Sheet

SECOSTEROIDS, AND METHOD FOR PRODUCING SAME

BACKGROUND OF THE INVENTION

A number of examples of secosteroid compounds which exhibit cytotoxic and ichthyotoxic activity have recently been isolated from various marine invertebrates (D'Auria, M. V., L. Minale, R. Riccio [1993] *Chem. Rev.* 93:1839). Secosteroids are a group of sterols structurally characterized by the absence of a bond in the nucleus. A group of three 9(11)-secosterols (formulae 1–3 in FIG. 1), isolated from marine organisms belonging to the genus Pseudopterogorgia, have been shown to be responsible for the chemical defense of the organism. For example, it has been demonstrated that secosteroids afford an efficient fish-feeding deterrent for the source gorgonian. Further, it has recently been demonstrated that certain 9(11)-secosterols (e.g., 1) exhibit inhibitory activity against protein kinase C and potent anti-proliferative and anti-inflammatory activity (He, H., P. Kulanthaivel, B. J. Baker, K. Kalter, J. Darges, D. Cofield, L. Wolff [1995] *Tetrahedron* 51:51). There can therefore be considerable utility for these sterols in the pharmaceutical industry.

As with the vast majority of marine-derived bioactive agents, 9(11)-secosteroids are sufficiently complex that a completely synthetic approach to their production is an expensive and time-consuming undertaking. For example, the current synthetic method for producing the 9(11)-secosteroid 4 (FIG. 1) from 7-dehydrocholesterol acetate involves a seven-step procedure requiring numerous HPLC purifications and an overall yield of ca. $4 \times 10^{-3}\%$ (Adinolfi, R., A. Miglinolo, V. Piccialli, D. Sica [1994] *J. Nat. Prod.* 57:1220). Besides synthetic procedures, compounds in the secosteroid class of steroids are generally collected from biomass, i.e., harvesting of source organisms for extraction therefrom. In the procedure involving collection from biomass, the pure steroid is obtained from a crude extract of the source organism by tedious chromatographic methods. A disadvantage of the biomass collection/purification procedure is that large quantities of organisms are required and are often obtained from sensitive marine habitats. Also, only the naturally-occurring steroids will be obtained. Therefore, there is a need in the pharmaceutical industry to produce secosterol compounds efficiently, inexpensively, and without causing undue stress or harm to the ecosystems or habitats of organisms that naturally produce these compounds.

BRIEF SUMMARY OF THE INVENTION

The subject invention concerns the identification and use of enzyme preparations obtained from marine organisms. In accordance with the teachings of the subject invention, these enzyme preparations can be used to economically and efficiently produce a variety of compounds having highly advantageous biological and/or pharmacological properties. By using the enzyme preparations of the subject invention, it is possible to mimic highly efficient natural enzymatic pathways in order to rapidly synthesize products which might otherwise require intricate synthetic schemes to produce. A further advantage resulting from the materials and methods provided herein is the ability to produce a wide variety of new compounds by using the enzyme preparations described herein with an assortment of substrates. This provides a powerful tool for generating libraries of compounds useful for assessing function/structure relationships as well as identifying new compounds with particularly advantageous biological properties.

Thus, in a most general sense, the subject invention provides methods for identifying, isolating, and using enzyme preparations from any appropriate marine organism. In a preferred embodiment, the enzyme preparation will be obtained from a marine organism which is known or suspected to produce a desired metabolite. The metabolite may have, for example, antiproliferative, antimicrobial, anti-inflammatory, and/or antiviral properties. By identifying and isolating enzyme preparations from the natural source of these active compounds, it is then possible to more easily and efficiently produce the active compounds, and derivatives and analogues of these compounds, in useful quantities. The use of these enzymes in semi-synthetic or bio-synthetic synthesis schemes reduces the need for designing intricate synthetic schemes. A further critical advantage provided by the subject invention is that the useful compounds produced using these enzyme preparations can be produced in large quantities without depleting our precious marine resources.

The marine organisms which can serve as the source for enzyme preparations useful according to the subject invention include, but are not limited to, coral (Cnidaria), sponges, sea squirts, algae, bacteria, and the like. A preferred source of the enzyme composition which can be used in accordance with the subject invention is coral, and more preferably, coral classified in the genus Pseudopterogorgia.

Although it is not necessary to identify with specificity the particular enzyme activities in the enzyme preparations of the subject invention, one embodiment of the subject invention involves identifying these enzymes, isolating the genes which encode the enzymes, and producing the enzymes recombinantly.

In a specific embodiment, the subject invention concerns a method for producing secosteroids from their corresponding steroid precursors. The method employs a composition comprising an enzyme, or a mixture of enzymes, capable of producing a wide range of 9(11)-secosterols in a single step. The subject method advantageously yields the desired secosteroids at percentage recovery levels acceptable to industrial application and can produce certain of the desired secosteroid compounds in high yields. The process is convenient and rapid and does not require extensive chromatographic separations as required in synthesis processes. The subject invention also includes enzyme compositions used in the subject methods.

One source of enzymes useful according to the subject invention is the gorgonian *Pseudopterogorgia spp.* For example, an enzyme composition useful for the subject invention has been obtained from the species *P. americana*. There are a number of "chemotypes" of gorgonians which have very similar morphologies to *P. americana*. These gorgonians having similar chemotypes can also comprise the enzymes employed in the enzyme composition useful for producing a secosteroid from its corresponding steroid according to the subject invention. Individual gorgonians can be assayed for the presence of secosteroids by thin layer chromatography.

A further aspect of the invention includes novel secosteroid compounds extracted from a natural source, e.g., a gorgonian, or that are produced by the subject method.

DETAILED DISCLOSURE OF THE INVENTION

Figure 1:
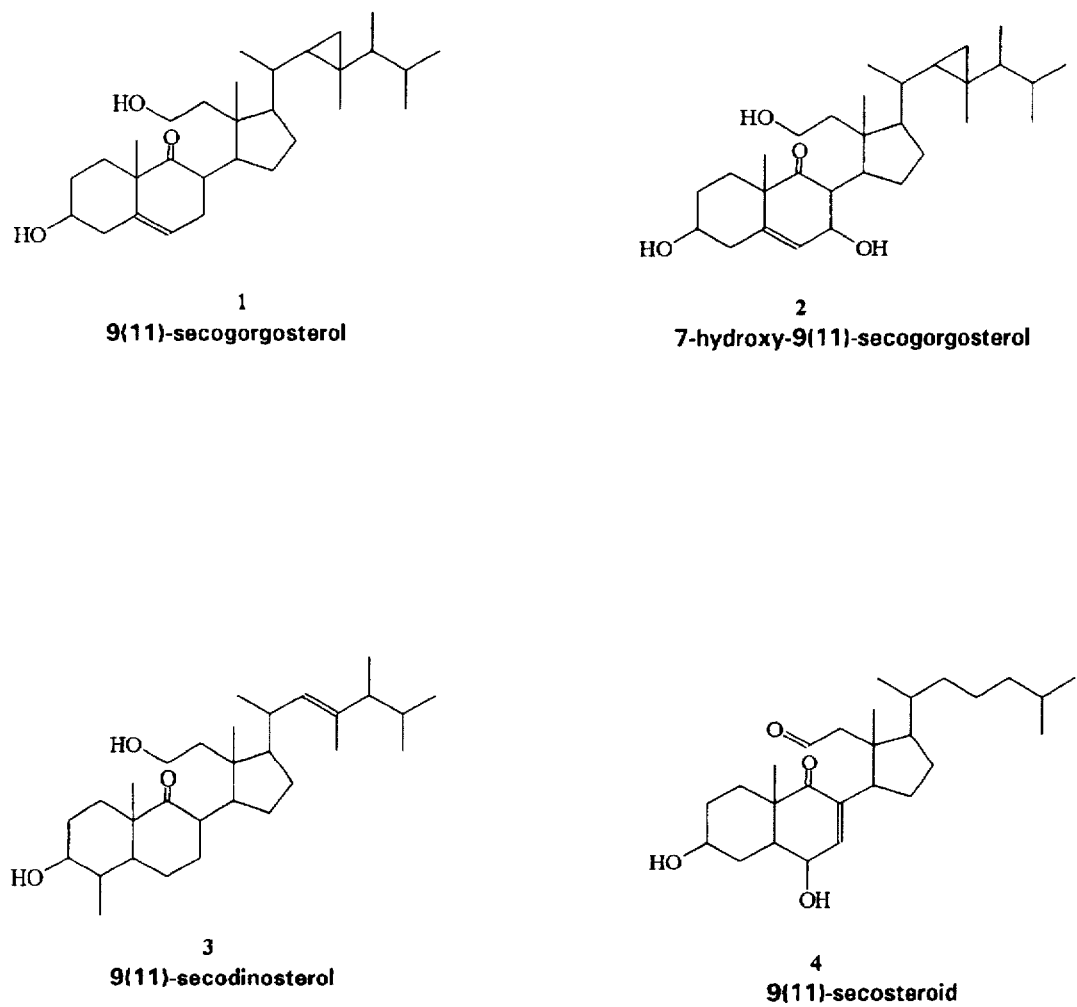
FIG. 1 shows the structures of secosterols 1 (9(11)-secogorgosterol), 2 (7-hydroxy-9(11)-secogorgosterol), 3 (9(11)-secodinosterol), and 4 (9(11)-secosteroid).

The subject invention concerns a unique preparation obtained from a marine source, wherein the preparation comprises at least one enzyme, or a mixture of more than one enzyme or enzymes, that are capable of converting a particular compound (a precursor) to its metabolite or derivative, which is the desired compound of interest. The subject invention also concerns the method of producing the compound or compounds of interest by employing the unique enzyme preparation or composition to carry out a reaction converting a metabolic precursor to a compound of interest. The method of preparing the enzyme composition which is used to carry out the reaction converting the precursor to the desired product is also considered to be part of the subject invention. Further, the method of using the enzyme composition can be used to yield novel compounds. These novel compounds, and compositions comprising those compounds, are also included in the subject invention.

In a specific embodiment, the subject invention concerns a method or process whereby a steroid compound can be converted to its secosteroid derivative using a composition comprising an enzyme or mixture of enzymes. The enzyme composition preferably can comprise certain co-factors or co-enzymes which can improve the efficiency or yield of the reaction. Other additives or ingredients can also be included in the enzyme composition. The enzymes useful for carrying out the reaction of converting a steroid to its corresponding secosteroid can be obtained from a natural source.

One method of the subject invention involves the following steps: (1) providing an enzyme composition capable of producing a secosteroid from its corresponding steroid precursor; and (2) adding the steroidal precursor to the enzyme composition to allow the conversion of steroid to its secosteroid derivative. The subject method can further include isolation and/or collection of the secosteroid products, using techniques which are readily apparent and understood by those of ordinary skill in the art having the benefit of the teachings provided herein. Further derivatization can be carried out on the secosteroid product using known procedures to yield additional secosteroid derivatives or analogues. The further derivatization of the secosteroid products from the subject enzymatic procedure can be used to produce secosteroid compounds which are either novel or known.

The enzymes for use in the enzyme extract of the subject invention can be obtained from a natural source, e.g., a marine organism. Other organisms, including other marine organisms such as sponges, sea squirts, algae, bacteria, and the like, can comprise useful enzymes for producing secosteroids from a steroid precursor, or other useful compounds. In addition, these marine organisms can be the source of other useful compounds, including bryostatin (an antileukemic or antimelanoma agent), ectinascidin (antitumor agent), stevensine (anticancer agent), cignatoxin (a seafood toxin), and others. These marine organisms can also be a source of enzymes for production of the useful compounds, whereby the enzymes can be employed in accordance with the subject invention. In a preferred embodiment, the subject enzymes for the extract can be obtained from a gorgonian coral. More preferably, the enzymes can be obtained from a gorgonian of the Pseudopterogorgia genus, e.g., P. americana.

A P. americana organism useful according to the subject invention can be obtained from the Florida coastal areas from West Palm Beach to the lower Keys at depths of about 1 to 30 meters.

The enzymes can be extracted from the source organism, e.g., coral, by homogenizing the organism or a collection of organisms in a phosphate buffer (pH=7.4–8.0), centrifuging at 5,000×g to remove insoluble debris, cold-centrifuging that supernate at 18,000×g for 1–2 hours, filtering the second supernate through filters having pore sizes of 0.45 μm and 0.2 μm, and precipitating the proteins by adding the resulting extract to cold acetone. The precipitate which comprises the enzymes of interest can be obtained by decanting the fluid, filtering, and washing with acetone, ether, or like solvents. A preferred embodiment of the above enzyme extraction procedure is described in Example 1. Other sources can also be available for the subject enzymes. Where a different organism is used for obtaining the enzymes of interest, the extraction procedures generally follow the steps outlined above, with any modifications due to the particular source organism being well within the understanding of those having ordinary skill in the art with the benefit of the current disclosure.

The enzyme extract can be used for the conversion of a sterol to its secosterol derivative, viz., its 9(11)-secosterol derivative. In a preferred embodiment, the enzyme extract can be fortified with co-enzyme NAD or NADP to produce the subject fortified enzyme composition. Fortification of the enzyme composition with both NAD and NADP is a preferred embodiment. In a most preferred embodiment, glutamate dehydrogenase can also be included in the fortified enzyme composition. In order to convert the sterol to its corresponding 9(11)-secosterol derivative, a single step of incubation of the sterol in the fortified enzyme composition for sufficient time to carry out the conversion reaction achieves the desired result of secosteroid production. In one embodiment, the precipitate of the subject enzyme extract can be dissolved in a phosphate buffer (pH=7.4–8.0) to produce a solution of the enzyme extract. The enzyme extract precipitate can be added to the buffer in amounts of about 200–250 mg/100 ml. The solution can then be fortified, preferably with NAD and NADP (4–5 mg each/100 ml), along with about 1 mg of glutamate dehydrogenase to produce a fortified enzyme composition.

The sterol can then be added to the fortified enzyme composition to carry out the conversion reaction to produce the corresponding secosteroid. Preferably, about 5 to about 25 mg of sterol can be added per 100 ml of the fortified enzyme composition. For conversion to the secosterol derivative, the sterol is incubated in the fortified enzyme composition for at least 24 hours, preferably at least 48 hours, but, preferably, not more than 72 hours. In a preferred embodiment, the conversion reaction from a sterol to a secosterol is carried out in a shaker water bath at a temperature of between 25°–40° C., preferably at about 30° C. The reaction can be quenched by immersion in liquid nitrogen, and the frozen fortified enzyme composition now comprising secosterol derivatives can be lyophilized and purified using standard and well-known chromatography, preferably thin-layer chromatography (TLC), techniques. A preferred procedure for converting a sterol to its 9(11)-seccosterol derivative is described in Example 2.

The subject enzymatic process can be used for the production of a wide range of novel 9(11)-secosterols. Secosteroids (1, 5–10), the formulae of which are shown below, have been confirmed as being produced from the enzymatic transformation of the subject invention.

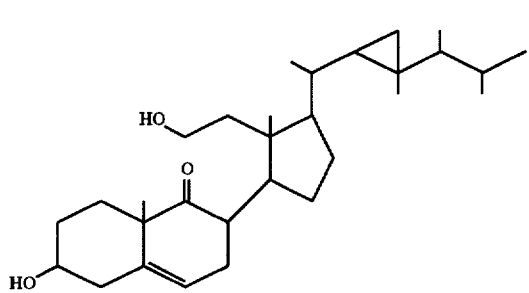

5

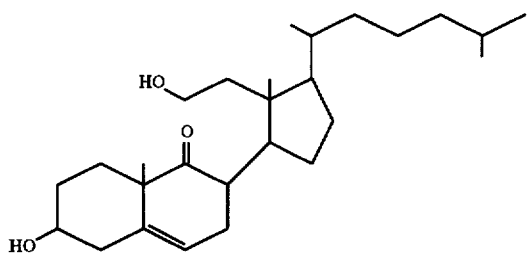

6

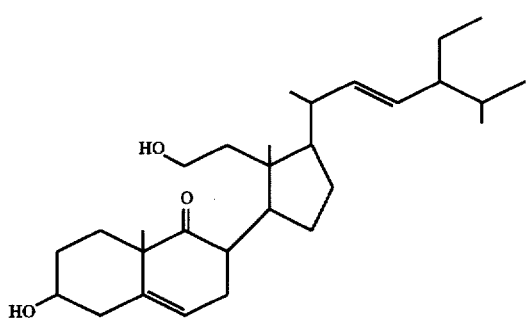

7

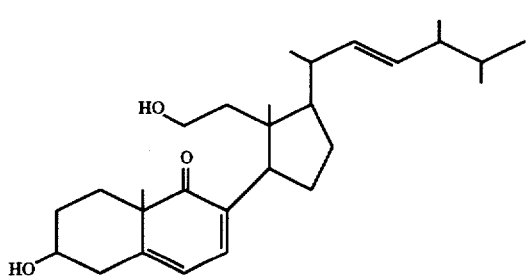

8

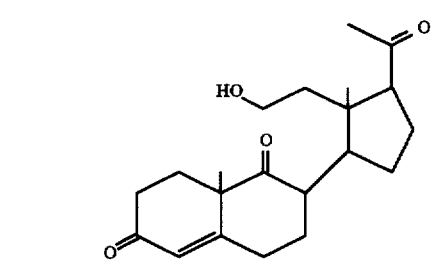

9

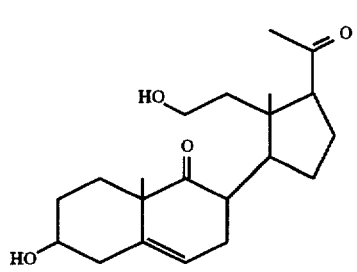

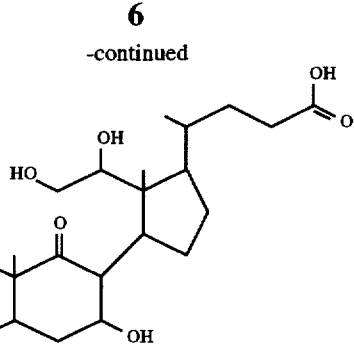

10

The yields vary from 15% to nearly 100% on scales of 5–25 mg. Specifically, the yield for compound 1 was nearly 100%; compound 5, 78%; compound 6, 18%; compound 7, 15%; compound 8, 24%; compound 9, 22%; and compound 10, 15%. It is believed that this is the first synthesis of a group of biologically active steroids using the enzymatic machinery of a marine invertebrate.

As a determination of substrate specificity, we examined the transformation of cholesterol, stigmasterol, ergosterol, pregnenolone, cholic acid, and progesterone, none of which are present in the gorgonian. All sterols were transformed to their 9(11)-seco derivatives. In addition to generating the secosteroids present in the gorgonian, the enzymatic process is applicable to the production of novel 9(11)-secosteroids. With the findings that progesterone, cholesterol, and stigmasterol were converted to their corresponding 9(11)-secosteroid derivatives using the fortified enzyme composition of the subject invention, it can be concluded that the subject method can be used for the production of a wide range of novel secosteroids.

Compounds 6–10 have not heretofore been described. Thus, the subject invention includes these novel compounds. These novel compounds can have utility as fish-feeding deterrents. In addition, those compounds which exhibit anti-inflammatory or antiproliferative activity can be useful in certain therapeutic or prophylactic treatments in patients having symptoms, conditions, or diseases that call for such activity. These compounds can also be included with a pharmaceutically acceptable carrier to produce a pharmaceutical composition for administering to a patient in need of such treatment.

Following are examples which illustrate procedures for practicing the invention. These examples should not be construed as limiting. All percentages are by weight and all solvent mixture proportions are by volume unless otherwise noted.

Example 1—Preparation of Enzyme Extract

A crude cell-free extract was prepared by adding 2 cm lengths of the freshly-collected gorgonian (100 g) to a Waring blender containing phosphate buffer at pH 7.7 (300 mL) and liquid nitrogen (100 mL). The mixture was blended for 2–4 minutes and was then centrifuged at 5,000×g to remove insoluble debris. The resulting supernatant was then subjected to centrifugation at 18,000×g at 0° C. for 1.5 hours followed by a second centrifugation of the supernatant under the same conditions. The resulting supernatant was then successively passed through 0.45 µm and 0.20 µm filters at ambient temperature. Proteins were precipitated by slowly adding the enzyme extract to vigorously stirred acetone at −70° C. The resulting white precipitate was decanted, filtered, and washed with cold acetone and ether. Filtration and washing with cold acetone afforded a white solid. The yield of protein precipitate varied somewhat between individual organisms; typically, this process generated 0.5 g acetone powder from 25 g of gorgonian. The acetone powder can be stored at −80° C. for at least six months with no loss in activity.

Example 2 —Production of Secosteroid Using Fortified Enzyme Composition

The transformation of a sterol to its 9(11)-seco derivative can be achieved as follows: The acetone powder (100 mg) was dissolved in 45 mL phosphate buffer (pH 7.7) and fortified with NAD (2 mg), NADP (2 mg), and glutamate dehydrogenase (0.5 mg). This mixture was then incubated with the sterol in a shaker water bath at 30° C. for 48 hours. The enzymatic reaction was then quenched by rapid immersion in liquid nitrogen. The frozen extract was subjected to lyophilization, and the secosteroid was purified by preparative TLC. The secosteroids from the TLC purification were found to be homogeneous by HPLC (C-18) and were characterized spectroscopically. The $^1$H-NMR of 1 was identical to that obtained from a standard sample isolated from the gorgonian.

Example 3 —Determination of Cofactor Requirement

To determine which cofactors were desirable for this oxidative process, portions of an acetone powder were incubated with gorgosterol under various conditions (see Table 1). Either NAD or NADP can be used to fortify the subject enzyme composition for effectively converting a steroid compound to its corresponding 9(11)-secosteroid. In a preferred embodiment of the subject invention both NAD and NADP can be used in the fortified enzyme composition. The use of both cofactors can produce optimal production of a secosteroid from its corresponding steroid used as a precursor. For example, as shown in Table 1, use of both NAD and NADP in the subject enzyme composition yields up to 97% product compared to a 50% yield using NAD alone or an 18% yield using NADP alone. Glutamate dehydrogenase can also be employed to regenerate the oxidized form of the coenzymes during the incubation. Thus, a most preferred embodiment of the subject fortified enzyme composition comprises glutamate dehydrogenase. The incubation time was determined from an incubation of cholesterol under the conditions described above, with aliquots being removed at various time intervals. Secosteroid production was found to reach a maximum at 48 hours and appeared to decline in longer incubations.

TABLE 1

Effects of co-factors on secosteroid production

| Trial | NAD (mg) | NADP (mg) | % yield of 9(11)-secogorgosterol |
|---|---|---|---|
| 1 | 2 | 0 | 50 |
| 2 | 0 | 2 | 18 |
| 3 | 2 | 2 | 97 |

Example 4—Formulation and Administration

The compounds of the invention are useful for various non-therapeutic and therapeutic purposes. The compounds of the invention can be effective for controlling inflammation and can have antiproliferative activity which has been shown to be useful in controlling tumor growth. At certain concentrations, the compounds or composition comprising these compounds can have antimicrobial or antiviral activity. Thus, the compounds can be used to inhibit unwanted bacterial or viral growth in the work areas of virology labs. Also, the compounds can be used as ultraviolet screeners in the plastics industry since they can effectively absorb UV rays. As disclosed herein, they can be used therapeutically for treating inflammation, treating tumors, or as immunomodulatory, antibacterial, or antiviral agents in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the secosterol compounds, e.g., a 9(11)-secosterol, as a first active ingredient plus a second active ingredient, e.g., an anti-inflammatory, antimicrobial, antiproliferative, or antiviral compound, known in the art. Known anti-inflammatory drugs include, but are not limited to, the steroidal anti-inflammatory drugs and the non-steroidal anti-inflammatory drugs (NSAIDs).

In accordance with this invention, pharmaceutically effective amounts of a known anti-inflammatory agent and the secosteroid compounds are administered sequentially or concurrently to the patient. The most effective mode of administration and dosage regimen of secosteroid compounds will depend upon the type of disease to be treated, the severity and course of that disease, previous therapy, the patient's health status, and response to secosteroids and the judgment of the treating physician. The secosteroid compositions may be administered to the patient at one time or over a series of treatments.

Preferably, the secosteroid and the second agent, e.g., the antimicrobial agent, are administered sequentially to the patient, with the second agent being administered before, after, or both before and after treatment with the secosteroid compound or composition. Sequential administration involves treatment with the second agent at least on the same day (within 24 hours) of treatment with secosterol may involve continued treatment with the second agent on days that the secosterol is not administered. Conventional modes of administration and standard dosage regimens for the subject secosteroid or a pharmaceutical composition comprising the secosteroid may be used (see Gilman, A. G. et al. [eds.] The Pharmacological Basis of Therapeutics, pp. 697–713, 1482, 1489–91 [1980]; Physicians Desk Reference, 1986 Edition), similar to other compounds used for the treatments. For example, indomethacin can be administered orally at a dosage of about 25–50 mg, three times a day. Higher doses can also be used. Alternatively, aspirin (about 1500–2000 mg/day), ibuprofen (about 1200–3200 mg/day), or conventional therapeutic doses of other anti-inflammatory agents can be used. Dosages of anti-inflammatory agents can be titrated to the individual patient.

According to one embodiment of this invention, the patient may receive concurrent treatments with compositions comprising a secosterol, e.g., a 9(11)-secosterol, and a second active ingredient. For example, local, intralesional, or intravenous injection of secosteroids is preferred (see Gilman et al., supra at pp. 1290–91) but can be administered by subcutaneous injection, subcutaneous slow-release implant, or orally.

Alternatively, the patient can receive a composition comprising a combination of one or more secosteroid compounds and second active agent according to conventional modes of administration of agents which exhibit antibacterial, anticancer, antitumor, or anti-inflammatory activity. These include, for example, enteric, parenteral, subcutaneous, intravenous, intramuscular, or intralesional routes of administration.

The compositions used in these therapies can also be in a variety of forms. These include, for example, solid, semi-solid, and liquid dosage forms, such as tablets, pills, powders, liquid solutions or suspension, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A method for producing a compound from its metabolic precursor, said method comprising:

(a) providing an enzyme composition capable of carrying out a metabolic reaction to convert a steroid metabolic precursor to a secosterol, wherein said enzyme composition is from a coral of the genus Pseudopterogorgia;

(b) adding the metabolic precursor to said enzyme composition;

(c) allowing said metabolic reaction to be carried out by the enzyme composition; and (d) collecting said secosteroid.

2. The method, according to claim 1, wherein said secosteroid is a 9(11)-secosteroid.

3. The method, according to claim 2, wherein said 9(11)-secosteroid is selected from the group consisting of

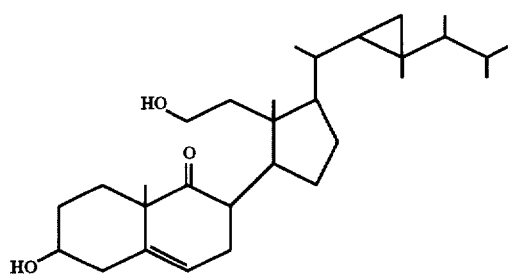

1

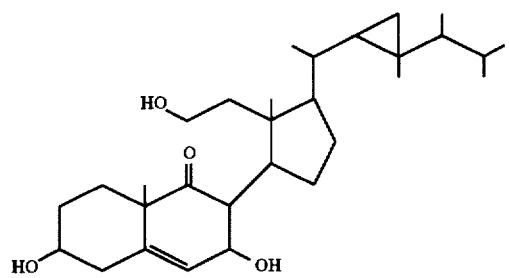

2

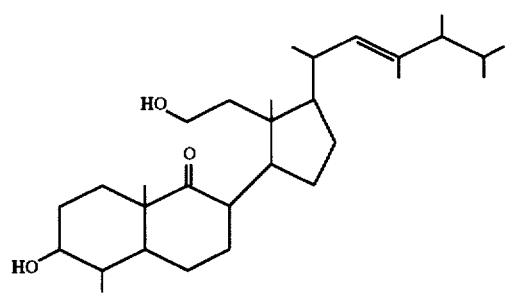

3

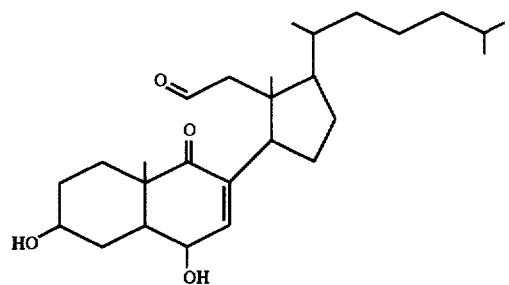

4

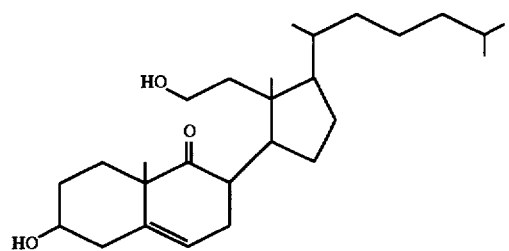

5

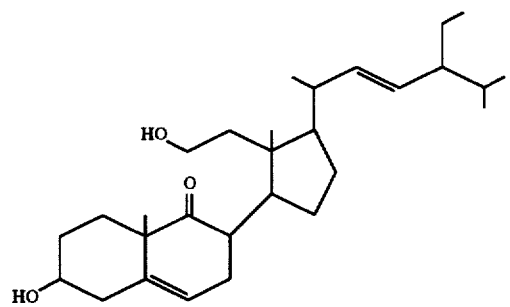

6

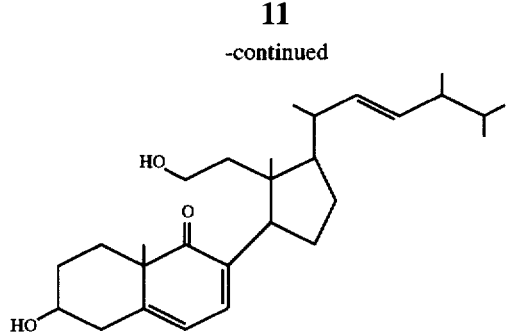
7
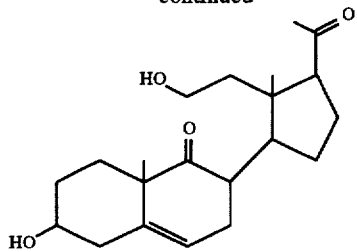
9
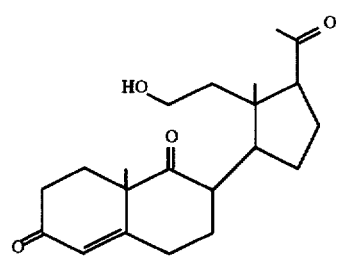
8
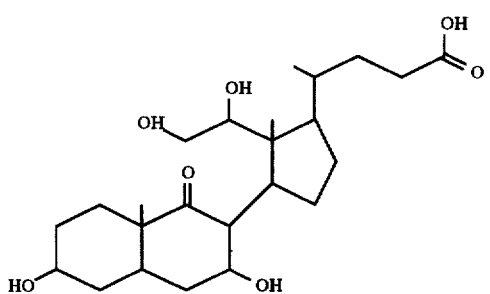
10
* * * * *